United States Patent

Yaso et al.

[11] Patent Number: 4,870,171
[45] Date of Patent: Sep. 26, 1989

[54] 1-SUBSTITUTED ALKYL-2-OXO-1,2-DIHYDROQUINOXALINE DERIVATIVES

[75] Inventors: Masao Yaso; Yukio Suzuki; Eiichi Honda; Kensuke Shibata; Hiroyuki Kinoshita; Noriyasu Takayanagi; Tetsu Saito; Eiichi Hayashi, all of Shizuoka, Japan

[73] Assignee: Toyo Jozo Kabushiki Kaisha, Shizuoka, Japan

[21] Appl. No.: 235,733

[22] Filed: Aug. 22, 1988

[30] Foreign Application Priority Data

Aug. 21, 1987 [JP] Japan .................. 62-207989

[51] Int. Cl.$^4$ .................. C07D 403/06; A61K 31/495
[52] U.S. Cl. ...................... 544/354; 544/395
[58] Field of Search ........................ 544/354

[56] References Cited

U.S. PATENT DOCUMENTS 4,262,123  4/1981  Hall et al. ............... 544/354
4,339,452  7/1982  Hara et al. ............... 514/249

FOREIGN PATENT DOCUMENTS 0008864  3/1980  European Pat. Off. .
0032564  7/1981  European Pat. Off. .

Primary Examiner—Mark L. Berch
Assistant Examiner—E. Bernhardt
Attorney, Agent, or Firm—Young & Thompson

[57] ABSTRACT

A compound of the formula

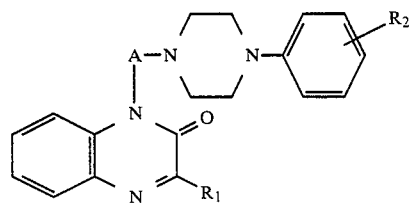

wherein $R^1$ is hydrogen or lower alkyl, $R^2$ is hydrogen, lower alkoxy or halogen, and A is lower alkylene, or a pharmacologically acceptable salt thereof, has sympatholytic α-receptor blocking activity and is useful for the treatment of hypertension.

3 Claims, No Drawings

1-SUBSTITUTED ALKYL-2-OXO-1,2-DIHYDROQUINOXALINE DERIVATIVES

FIELD OF THE INVENTION

This invention relates to novel 1-substituted alkoxy-2-oxo-1,2-dihydroquinoxaline derivatives having sympatholytic α-receptor blocking activity, and which are useful for the treatment of hypertension.

THE PRIOR ART

Hitherto known 1-substituted-2-oxo-3-substituted-1,2-dihydroquinoxaline derivatives having pharmacological activity are: 1-(amino, lower alkylamino or di-lower alkylamino)-lower alkyl-2-oxo-3-lower alkyl-1,2-dihydroquinoxaline, which is useful as a tranquilizer (Jap. Pat. Publ. No. 45-19907); 1-diethylaminoethyl-2-oxo-3-(benzyl or substituted benzyl)-1,2-dihydroxyquinoxaline, which has antispasmolytic or platelet aggregation activity (Jap. Pat. Publ. No. 46-11183, Jap. Pat. Unexam. Publ. No. 56-97226 and No. 56-97228); 1-alkyl-2-oxo-3-substituted carbamoyloxymethyl-1,2-dihydroquinoxaline, which is effective for the treatment of arteriosclerosis and thrombosis (Jap. Pat. Unexam. Publ. No. 49-24981); 1-alkyl-2-oxo-3-(tetrazole-5-yl carbamoyl)-1,2-dihydroquinoxaline, which is useful for the treatment of extrinsic asthma and urticaria (Jap. Pat. Unexam. Publ. No. 50-29583); 1-substituted phenyl-2-oxo-3-(alkyl, carboxyalkyl or dicarboxyalkyl)-1,2-dihydroquinoxaline, which is useful for the treatment of inflammation and rheumatoid arthritis (Jap. Pat. Unexam. Publ. No. 55-115875); and 1-(phenyl or substituted phenyl)-2-oxo-3-(amino or alkaneamide) 1,2-dihydroquinoxaline-4-oxide, which has antispastic activity, ataractic activity or psycholeptic activity (Jap. Pat. Unexam. Publ. No. 56-92277).

Other quinoxaline derivatives are known, which are useful for the treatment of hypertension, i.e. 1-isopropyl-amino-3-[2-(2-quinoxalyl) phenyl]-2-propanol (Jap. Pat. Publ. No. 43-9220), 2-methyl-3-[2-(4-phenyl or tryl)-piperazinyl]ethoxyquinoxaline (Jap. Pat. Publ. No. 48-21949), 5-halogeno-6-(2-imidazolin-2-yl-amino) quinoxaline (Jap. Pat. Unexam. Publ. No. 48-97878), 2-methyl-3-(2-hydroxyquinoxaline-6 or 7-yl) alanine (Jap. Pat. Unexam. Publ. No. 52-97933), 5- or 8-(2-hydroxy-3-substituted amino-propoxy)-2-oxo-3-methyl quinoxaline (Jap. Pat. Unexam. Publ. No. 55-162783) and 4-fluoro-N-{2-[4-(5-quinoxalyl)-1-piperazinyl] ethyl} benzamide (Jap. Pat. Unexam. Publ. No. 60-104063).

BRIEF SUMMARY OF THE INVENTION

The present invention provides compounds of the formula

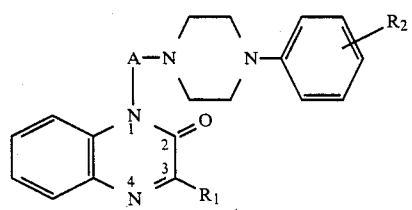

[1]

wherein $R_1$ is hydrogen or lower alkyl, $R_2$ is hydrogen, lower alkoxy or halogen, and A is lower alkylene, or a pharmacologically acceptable salt thereof.

DETAILED DESCRIPTION OF THE INVENTION

The compounds [1] can be produced by the following process:

A compound [1] can be produced by reacting a 2-oxo1,2-dihydroquinoxaline derivative of the formula

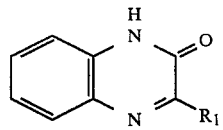

[2]

wherein $R_1$ has the same meaning hereinabove, with a hydroxyalkyl halide of the formula

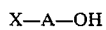

wherein X is halogen and A has the same meaning hereinabove, in an organic solvent, to obtain a 1-hydroxyalkyl-2-oxo-1,2-dihydroquinoxaline derivative of the formula

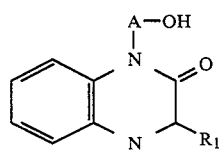

[3]

wherein $R_1$ and A have the same meanings hereinabove, then halogenating the said compound [3] with a halogenating agent to obtain a 1-halogenoalkyl-2-oxo-1,2-dihydroquinoxaline of the formula

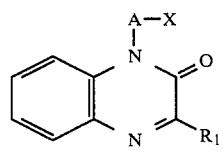

[4]

wherein X is halogen, and $R_1$ and A have the same meanings hereinabove, thereafter reacting the said compound [4] with an amine of the formula

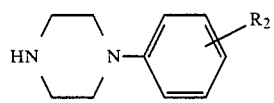

[5]

wherein $R_2$ has the same meaning hereinabove, in the presence of a base in an organic solvent.

In the compound [2] hereinabove, $R_1$ is hydrogen or lower alkyl. The above alkyl means alkyl of $C_{1-4}$ which may optionally be branched. Examples are methyl, ethyl, propyl, isopropyl, butyl, isobutyl, sec-butyl or t-butyl. The above compounds [2] can be produced by a known process disclosed in J. Am. Chem. Soc., 75: 328 (1953) and ibid. 76: 287 (1954).

A group A in the above hydroxyalkyl halide is lower alkylene. Examples of lower alkylene are methylene, ethylene, methylmethylene, propylene, 1-methylethylene, dimethylethylene or 1-ethylmethylene. Ethylene is preferred.

A group X in the above hydroxyalkyl halide is halogen such as chlorine or bromine, and in general chlorine is preferred. The preferred compound is ethylene chlorohydrine.

A reaction of the compound [2] with hydroxyalkyl halide proceeds in an organic solvent such as t-butanol.

The above reaction proceeds preferably in an aqueous alkali such as hydroxy alkali, and preferably is possible with heating. Isolation of the compound [3] can be performed by adding water to the reaction mixture and extracting it with a water-immiscible organic solvent.

The above compound [4] can be produced by halogenating the compound [3] hereinbefore with a halogenating agent.

Examples of the said halogenating agent are known halogenating agents. Conventional chlorination reagents such as $SOCl_2$, $PCl_5$ or $POCl_3$ can be used. The halogenation reaction can be conducted, in general, in an inert organic solvent such as chloroform. The reaction proceeds at room temperature. Separation of the product [4] can be effected by adding a water-immiscible organic solvent such as chloroform, washing with dilute aqueous alkali, dehydrating the organic layer and removing the solvent therefrom.

The compound [4] can be purified, if required, as by silica-gel column chromatography.

A compound [1] can be produced by reacting a compound [4] with an amine [5].

The group $R_2$ in the above amine [5] is hydrogen, lower alkoxy or halogen. Examples of the above lower alkoxy are alkoxys of $C_4$ which may optionally be branched, such as methoxy, ethoxy, propoxy, isopropoxy, 1-methylethoxy, butoxy, isobutoxy, sec-butoxy or t-butoxy. An example of the halogen is chlorine.

Accordingly, examples of the amine [5] are 4-phenyl-piperazine, 4-(o-, m- or p-chlorophenyl)-piperazine and 4-(o-, m- or p-methoxyphenyl)-piperazine.

The reaction of the compound [4] and the amine [5] hereinabove can conventionally be conducted in an inert organic solvent such as benzene with heating. In this reaction, hydrogen halogenide is generated so that the said reaction proceeds in the presence of an acid binder, for example a known tertiary organic amine such as triethylamine. The compound [1] can be isolated by pouring the reaction mixture into dilute aqueous alkali and extracting with a water-immiscible organic solvent such as benzene or chloroform.

The thus-obtained compound [1] is purified, if required, by column chromatography using silica gel, activated alumina or an adsorption resin, with an elution solvent such as chloroform-methanol or benzene-ethyl acetate.

A compound [1] is generally produced in the form of the free base, but it can be produced in the form of a conventional pharmacologically acceptable salt thereof. For example, the hydrochloride can be prepared by dissolving compound [1] in a lower alcohol such as methanol or ethanol, adding a calculated molar amount of hydrochloric acid, and isolating the precipitated material, or if not precipitated, by adding ether thereto to precipitate the salt. Other suitable salts are salts of inorganic acids such as sulfate and phosphate, and salts of organic acids such as acetate, propionate, glycolate, gluconate, malate, tartrate, succinate, mandelate, glutamate, aspartate, methanesulfonate and toluenesulfonate.

Pharmacological activities of the present compounds [1] are illustrated hereinbelow.

A test sample is prepared by dissolving a compound in the examples in a small amount of methanol, adding a two-molar amount of hydrochloric acid in methanol to precipitate the material, or if not precipitated, adding diethyl ether thereto to precipitate it, filtrating the precipitate, and drying the filtered precipitate in vacuo to obtain the dihydrochloride. The thus-obtained test sample is dissolved in distilled water or physiological saline before using.

1. α-blocking action:

Rat, Wistar, male, body weight 200 g, is sacrificed by bleeding. The extirpated spermatic duct is hung in Tyrode's solution at 37° C. The specimen duct is loaded at 0.5 g tension and a mixed gas of oxygen-carbon dioxide (95:5) is bubbled through the solution.

A constrictor, noradrenaline, $2 \times 10^{-5}M$ is added to the nutrient solution to constrict the spermatic duct. At the maximum constriction, the spermatic duct is washed with nutrient solution, and this operation is repeated at 20-minute-intervals until a constant constriction is observed. Thereafter, a test compound, which is used after dissolving and diluting with distilled water, is added to the nutrient solution, and after three minutes noradrenaline is added to constrict the duct specimen. The reaction is recorded under isotonic conditions. The suppressive ratio (%) is calculated as the ratio of suppression on the constriction with the test compound to the constriction when adding noradrenaline. The results are shown in Table 1.

Then the constrictor noradrenaline is replaced by barium chloride $(2 \times 10^{-3}M)$, and the results are also shown in Table 1. As is shown in the Table, since the test sample does not show the suppressive action against constriction for barium chloride at $10^{-6}$ g/ml, the above constriction suppressive action by noradrenaline is not based upon a non-specific smooth muscle suppression, but is an α-receptor activity.

TABLE 1

Test compound: 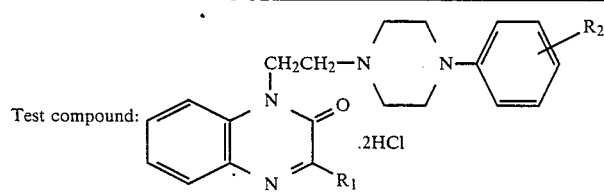

| Compound of the present invention | | Suppressive ratio (%) | | | | | |
|---|---|---|---|---|---|---|---|
| | | noradrenaline | | | | | barium chloride |
| No. of Example | $R_1$ | $R_2$ ( ): substituted position | concentration of test compound (g/ml) | | | | |
| | | | $10^{-9}$ | $10^{-8}$ | $10^{-7}$ | $10^{-6}$ | $10^{-5}$ | $10^{-6}$ |
| 1 | H | $-OCH_3$ (o) | -3.1 | 30.8 | 96.0 | | | -3 |

TABLE 1-continued

Test compound: [structure: CH₂CH₂-N-piperazinyl-phenyl-R₂ attached to 2-oxo-1,2-dihydroquinoxaline with R₁, ·2HCl]

| Compound of the present invention | | | | Suppressive ratio (%) | | | | | | |
|---|---|---|---|---|---|---|---|---|---|---|
| | | | | noradrenaline | | | | | | barium chloride |
| No. of | R₁ | R₂ | | concentration of test compound (g/ml) | | | | | | |
| Example | | ( ): substituted position | | $10^{-9}$ | $10^{-8}$ | $10^{-7}$ | $10^{-6}$ | $10^{-5}$ | | $10^{-6}$ |
| 2 | H | —OCH₃ | (m) | | | 1.0 | 68.3 | 98.0 | | |
| 3 | H | —OCH₃ | (p) | | | −2.0 | 26.3 | 88.3 | | |
| 4 | H | —Cl | (o) | −0.3 | 19.0 | 89.8 | | | | −8 |
| 5 | H | —Cl | (m) | | 1.0 | 27.0 | 91.5 | | | |
| 6 | H | —Cl | (p) | | | 24.8 | 81.8 | 97.3 | | |
| 7 | CH₃ | —OCH₃ | (o) | 0.8 | 32.8 | 98.8 | | | | −6 |
| 8 | CH₃ | —Cl | (p) | | −0.3 | 23.0 | 85.5 | | | |
| 9 | CH₃ | H | | | 6.8 | 43.5 | 99.8 | | | |

2. Hypotensive action:

Rat, Wistar, male, body weight 320–430 g, is anesthetized with urethane (1.0 g/kg, i.p.). Blood pressure is measured with a pressure-transducer by cannulation in the femoral artery.

A test compound, which is dissolved and diluted in physiological saline before using, is administered at 0.05 ml/100 g body weight through a cannula in the femoral artery.

The test compound obtained in Example 4 showed a hypotensive action of approximately 30% at 10 μg/kg administration, and approximately 40% at 100 μg/kg, which continued for 60 minutes after administration.

The test compound obtained in Example 7 showed the same level of hypotensive activity as the compound of Example 4. The maximum hypotensive activity of the test compound in Example 7 is slightly greater than that of Example 4; however the duration of activity is less than that of Example 4 at 100 μg/kg in the administered group.

The following examples illustrate the present invention:

EXAMPLES 1-6

1-(2-hydroxyethyl)-2-oxo-1,2-dihydroquinoxaline, which is a species of compound [3] above, is produced by adding 2-hydroxyquinoxaline (7.31 g, 50 mM) and 5N-NaOH (50 ml) to t-butanol (150 ml). Ethylene chlorohydrine (20.13 g, 0.25 M) was added thereto and the mixture was stirred at 60° C. for 165 mins. The organic solvent was removed in vacuo. Water was added to the residue, which was then extracted with chloroform (once with 250 ml and twice with 50 ml). The combined chloroform layer was dried with anhydrous sodium sulfate and concentrated in vacuo. The residue was charged on a column of silica gel (Wakogel C-200, Wako Pure Chem. Co.) and eluted with chloroform-methanol (50:1) to obtain 1-(2-hydroxyethyl)-2-oxo-1,2-dihydroquinoxaline (8.11 g, yield: 85.4%).

NMR ($\delta_{CDCl_3}^{TMS}$): 2.67 (1H, t, J=6), 3.8–4.2 (2H, m), 4.3–4.6 (2H, m), 7.2–8.0 (4H, m), 8.27 (1H, s) ppm Mass (CI): 191 (M⁺ +1), 173

IR (Nujol): 1645; 1605; 1590 cm⁻¹

1-[2-(4-substituted phenylpiperazinyl) ethyl]-2-oxo-1,2-dihydroquinoxaline, which is a species of compound [1] above, was produced by adding thionylchloride (0.42 ml) dropwise with ice cooling to the above 1-(2-hydroxyethyl)-2-oxo-1,2-dihydroquinoxaline (0.95 g, 5 mM) dissolved in chloroform (10 ml), and the mixture was stirred at room temperature to promote chlorination. Benzene (30 ml) and triethylamine were added to the reaction mixture, and further triethylamine (10 mM) was added and the material was refluxed. Dilute aqueous potassium carbonate was added to the reaction mixture and the mixture was extracted with chloroform. The extract was dried with anhydrous sodium sulfate and concentrated in vacuo. The residue was dissolved in a small amount of chloroform and was charged on a column of silica gel (C-200, 80 g) and eluted with chloroform-methanol to obtain 1-[2-(4-substituted phenylpiperazinyl) ethyl]-2-oxo-1,2-dihydroquinoxaline. Table 2 illustrates the chlorination time, the kind of amine, its amount used, the amount of triethylamine used, the reflux time, the ratio of eluant and the yields.

TABLE 2

Test compound:

CH₂CH₂—N(piperazinyl)—N-phenyl-R₂ attached to quinoxalin-2(1H)-one amine: HN(piperazinyl)—N-phenyl-R₂

| Example | Chlorination time (h) | ( ): salt | amount used | trietylamine (ml) | reflux time (h) | ratio of eluant | Yield (g) | Yield (%) |
| --- | --- | --- | --- | --- | --- | --- | --- | --- |
| 1 | 8  | o-OCH₃     | 1.92 | 2.8 | 14 | 500:1  | 0.38 | 20.0 |
| 2 | 14 | m-OCH₃     | 1.92 | 2.8 | 8  | 500:1  | 0.38 | 20.0 |
| 3 | 8  | p-OCH₃     | 1.92 | 2.8 | 14 | 500:1  | 0.24 | 13.2 |
| 4 | 14 | o-Cl (2HCl)| 2.70 | 4.2 | 8  | 1000:1 | 0.45 | 24.4 |
| 5 | 8  | m-Cl (2HCl)| 2.70 | 4.2 | 14 | 1000:1 | 0.47 | 25.5 |
| 6 | 14 | p-Cl (2HCl)| 2.70 | 14  | 8  | 1000:1 | 0.08 | 4.3  |

NMR ($\delta_{CDCl_3}^{TMS}$) and Mass (CI) spectra are shown in the following:

Compound of Example 1:
NMR: 2.6–2.9 (6H, m), 3.9–3.2 (4H, m), 3.86 (3H, s), 4.45 (2H, t, J=8), 6.7–8.0 (8H, m), 8.30 (1H, s) ppm
Mass: 365, 205

Compound of Example 2:
NMR: 2.6–2.9 (6H, m), 3.0–3.3 (4H, m), 3.79 (3H, s), 4.44 (2H, t, J=8), 6.5–6.6 (3H, m), 7.00–8.0 (5H, m), 8.30 (1H, s) ppm
Mass: 365, 205

Compound of Example 3:
NMR: 2.6–2.9 (6H, m), 2.9–3.2 (4H, m), 3.77 (3H, s), 4.44 (2H, t, J=8), 6.7–7.0 (4H, m), 7.2–8.0 (4H, m), 8.30 (1H, s) ppm
Mass: 365, 205

Compound of Example 4:
NMR: 2.6–2.9 (6H, m), 2.9–3.2 (4H, m), 4.45 (2H, t, J=8), 6.8–8.0 (8H, m), 8.31 (1H, s) ppm
Mass: 371, 369, 211, 209

Compound of Example 5:
NMR: 2.6–2.9 (6H, m), 3.0–3.3 (4H, m), 4.44 (2H, t, J=8), 6.6–8.0 (8H, m), 8.30 (1H, s) ppm
Mass: 371, 369, 211, 209

Compound of Example 6:
NMR: 2.6–2.9 (6H, m), 3.0–3.3 (4H, m), 4.44 (2H, t, J=8), 6.7–8.0 (8H, m), 8.30 (1H, s) ppm
Mass: 371, 369, 211, 209

EXAMPLES 7-9

1-(2-hydroxyethyl)-2-oxo-3-methyl-1,2-dihYdroquinoxaline, which is another species of compound [3] above, is produced by adding 3-methyl-2-hydroxyquinoxaline (4.8 g, 30 mM) to t-butanol (90 ml). 5-N NaOH (30 ml) was added thereto, and the mixture was heated at 6° C. Ethylene chlorohydrine (10.2 ml, 150 mM) was added thereto and the mixture was stirred at 60° C. for 3–4 hours. Precipitated byproduct was removed by filtration and the filtered solution was concentrated in vacuo, and the residue was extracted with chloroform (100 ml) and water (100 ml). The aqueous layer was extracted several times with chloroform (100 ml). The combined chloroform layer was dried with anhydrous sodium sulfate and concentrated in vacuo. Acetone (150 ml) was added to the residue, which was heated and then cooled to effect recrystallization to obtain 1-(2-hydroxyethyl)-2-oxo-3-methyl-1,2-dihydroquinoxaline as acicular crystals. Yield: 5.19 g (85.5%).

NMR ($\delta_{CDCl_3}^{TMS}$): 2.57 (3H, s), 4.05 (2H, t, J=5.5), 4.50 (2H, t, J=5.5), 7.2–7.86 (4H, m) ppm
IR (Nujol): 1645; 1610 (amino) cm⁻¹

1-[2-(4-substituted phenylpiperazinyl) ethyl]-2-oxo-3-methyl-1,2-dihydroquinoxaline, which is another species of compound [1] above, was produced by adding thionylchloride (0.44 ml, 6 mM) with ice cooling to the above 1-(2-hydroxyethyl)-2-oxo-3-methyl-1,2-dihydroquinoxaline (1.02 g, 5 mM) dissolved in chloroform (15 ml), and the mixture was stirred at room temperature for 4–6 hours. Benzene (20 ml) and triethylamine (4.18 ml, 30 mM) were added to the reaction mixture, and further triethylamine (10 mM) was added and the mixture was refluxed for 24 hours. The reaction mixture was concentrated in vacuo and chloroform (60 ml) and water (100 ml) were added to the residue, then the mixture was extracted with chloroform. The water layer was extracted 2–3 times with chloroform (60 ml). The combined extract was dried with anhydrous sodium sulfate and concentrated in vacuo. The residue, dissolved in a small amount of chloroform, was charged on a column of silica gel (C-200, 160 g) and eluted with chloroform-methanol (200:1) to obtain 1-[2-(4-substituted phenylpiperazinyl) ethyl]-2-oxo-1,2-dihydroquinoxaline.

Table 3 illustrates the kind of amine, its amount used and the yields.

TABLE 3

Compound:

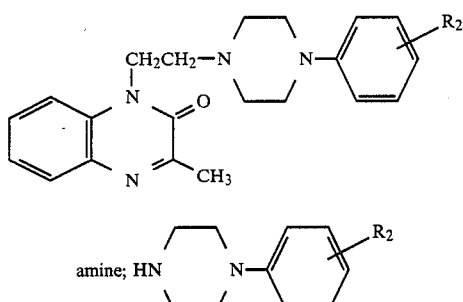

amine;

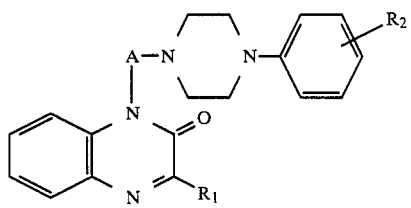

| Example | Amine R₂ ( ): salt | amount used (g) | yield (%) | yield (%) |
|---|---|---|---|---|
| 7 | o-OCH₃ | 1.92 | 1.02 | 27.0 |
| 8 | p-Cl (2HCl) | 2.70 | 0.22 | 5.8 |
| 9 | H | 1.53 | 0.73 | 42.0 |

NMR ($\delta_{CDCl_3}^{TMS}$) and Mass (CI) spectra are shown in the following:

Compound of Example 7:
NMR: 2.60 (3H, s), 2.77 (2H, t, J=7.6), 2.81 (4H, t, J=3.7), 3.13 (4H, t, J=3.7), 3.86 (3H, s), 4.45 (2H, t, J=7.6), 6.81–7.87 (8H, m) ppm
Mass: 379 (M⁺ +1), 219, 205, 187

Compound of Example 8:
NMR: 2.60 (3H, s), 2.75 (2H, t, J=7.0), 2.75 (4H, t, J=5.3), 3.18 (4H, t, J=5.3), 4.45 (2H, t, J=7), 6.77–7.86 (8H, m) ppm
Mass: 385, 383, 223, 209, 187

Compound of Example 9:
NMR: 2.60 (3H, s), 2.77 (2H, t, J=7.5), 2.74 (4H, t, J=5.3), 3.23 (4H, t, J=5.3), 4.46 (2H, t, J=7.5), 6.85–7.86 (9H, m) ppm
Mass: 349 (M₊ +1), 188

What is claimed is:

1. A compound of the formula wherein R¹ is hydrogen or lower alkyl, R₂ is hydrogen, lower alkoxy or halogen, and A is lower alkylene, or a pharmacologically acceptable salt thereof.

2. A compound of claim 1, wherein A is ethylene and R₁ is methyl.

3. A compound of claim 2, wherein R₂ is hydrogen, methoxy or chlorine.

* * * * *